United States Patent
Kovtunov et al.

(10) Patent No.: US 9,702,946 B1
(45) Date of Patent: Jul. 11, 2017

(54) CREATION OF LONG-LIVED SINGLET STATES OF GASES AND THEIR USE AS INHALABLE MRI CONTRAST AGENTS

(71) Applicant: Konstantin Saprygin, Moscow (RU)

(72) Inventors: Kirill V. Kovtunov, Novosibirsk (RU); Igor V. Koptyug, Novosibirsk (RU)

(73) Assignee: Konstantin Saprygin, Moscow (RU)

( * ) Notice: Subject to any disclaimer, the term of this patent is extended or adjusted under 35 U.S.C. 154(b) by 264 days.

(21) Appl. No.: 14/689,679

(22) Filed: Apr. 17, 2015

Related U.S. Application Data

(60) Provisional application No. 61/991,725, filed on May 12, 2014.

(51) Int. Cl.
| | |
|---|---|
| *A61B 5/055* | (2006.01) |
| *G01R 33/28* | (2006.01) |
| *A61K 49/10* | (2006.01) |
| *B01J 19/08* | (2006.01) |
| *A61K 49/04* | (2006.01) |

(52) U.S. Cl.
CPC ............ *G01R 33/282* (2013.01); *A61K 49/10* (2013.01); *B01J 19/087* (2013.01); *A61K 49/04* (2013.01); *B01J 2219/085* (2013.01)

(58) Field of Classification Search
None
See application file for complete search history.

(56) References Cited

U.S. PATENT DOCUMENTS

2006/0127313 A1* 6/2006 Goldman ............... A61K 49/10
424/9.3

OTHER PUBLICATIONS

Telkki et al. (Angew. Chem. Int. Ed. 2010, 49, 8363-8366).*
Bouchard et al. (Angew. Chem. Int. Ed. 2007, 46, 4064-4068).*
Burueva et al., Extending the Lifetime of Hyperpolarized Propane Gas through Reversible Dissolution, J. Phys. Chem., 4481-4487 (2017).
Burueva et al., Extending the Lifetime of Hyperpolarized Propane Gas Via Reversible Dissolution, J. Phys. Chem., 4481-4487 (2017), Supporting S1-57.
Barskiy et al., NMR Spin-Lock Induced Crossing (SLIC) dispersion and long-lived spin states of gaseous propane at low magnetic field (0.05 T), Journal of Magnetic Resonance 276 (2017) 78-85.
Barskiy et al., NMR Spin-Lock Induced Crossing (SLIC) dispersion and long-lived spin states of gaseous propane at low magnetic field (0.05 T), Journal of Magnetic Resonance 276 (2017) 78-85, Supporting S1-S11.
Salnikov et al., Efficient Batch-Mode Parahydrogen-Induced Polarization of Propane, ChemPhysChem 2016, 17, 3395-3398.
Salnikov et al., Efficient Batch-Mode Parahydrogen-Induced Polarization of Propane, ChemPhysChem 2016, 17, 3395-3398, Supporting S1-S6.
Barskiy et al., NMR SLIC Sensing of Hydrogenation Reactions Using Parahydrogen in Low Magnetic Fields, J. Phys. Chem. C 2016, 120, 29098-29106.

* cited by examiner

*Primary Examiner* — Michael G Hartley
*Assistant Examiner* — Melissa Perreira
(74) *Attorney, Agent, or Firm* — Bardmesser Law Group

(57) ABSTRACT

Parahydrogen Induced Polarization was employed to prepare nuclear singlet state between methylene and methyl protons in propane gas. Low-field MRI preserves this singlet state with much longer $T_S$=4.7±0.5 s. Spin-Lock Induced Crossing (SLIC) transforms singlet state in observable nuclear magnetization suitable for MRI with sub-millimeter and sub-second spatial and temporal resolution respectively with signal enhancement>10,000 times. Long-lived spin states created in hyperpolarized propane-$d_6$ gas can be detected directly at 0.0475 T. This long lifetime and non-toxic nature of propane gas could be useful for bio-imaging applications including potentially pulmonary low-field MRI. The feasibility of high-resolution low-field 2D gradient-echo MRI was demonstrated with 0.88×0.88 mm² spatial and ~0.7 s temporal resolution respectively at 0.0475 T. Propane is a non-toxic gas, and therefore, these results enable low-cost high-resolution high-speed MRI of gases for imaging of lungs.

15 Claims, 8 Drawing Sheets

CREATION OF LONG-LIVED SINGLET STATES OF GASES AND THEIR USE AS INHALABLE MRI CONTRAST AGENTS

CROSS-REFERENCE TO RELATED APPLICATIONS

This application is a non-provisional of U.S. Provisional Patent Application No. 61/991,725, filed on May 12, 2014.

BACKGROUND OF THE INVENTION

Hyperpolarized noble gases can be obtained by the process of spin-exchange optical pumping (SEOP). However, commonly used hyperpolarized (HP) gases, such as $^{129}$Xe, $^3$He, etc. are (i) significantly more expensive to begin with (cost of materials), (ii) require very expensive hyperpolarization equipment, and (iii) specialized RF hardware and MRI software for imaging. (ii) and (iii) in particular limited such promising technology to a few sites globally for functional lung MRI use.

Accordingly, there is a need in the art for cheaper and more readily available alternatives to $^{129}$Xe, $^3$He and similar gases.

BRIEF DESCRIPTION OF THE ATTACHED FIGURES

The accompanying drawings, which are included to provide a further understanding of the invention and are incorporated in and constitute a part of this specification, illustrate embodiments of the invention and together with the description serve to explain the principles of the invention.

DETAILED DESCRIPTION OF EMBODIMENTS OF THE INVENTION

Figure 1:
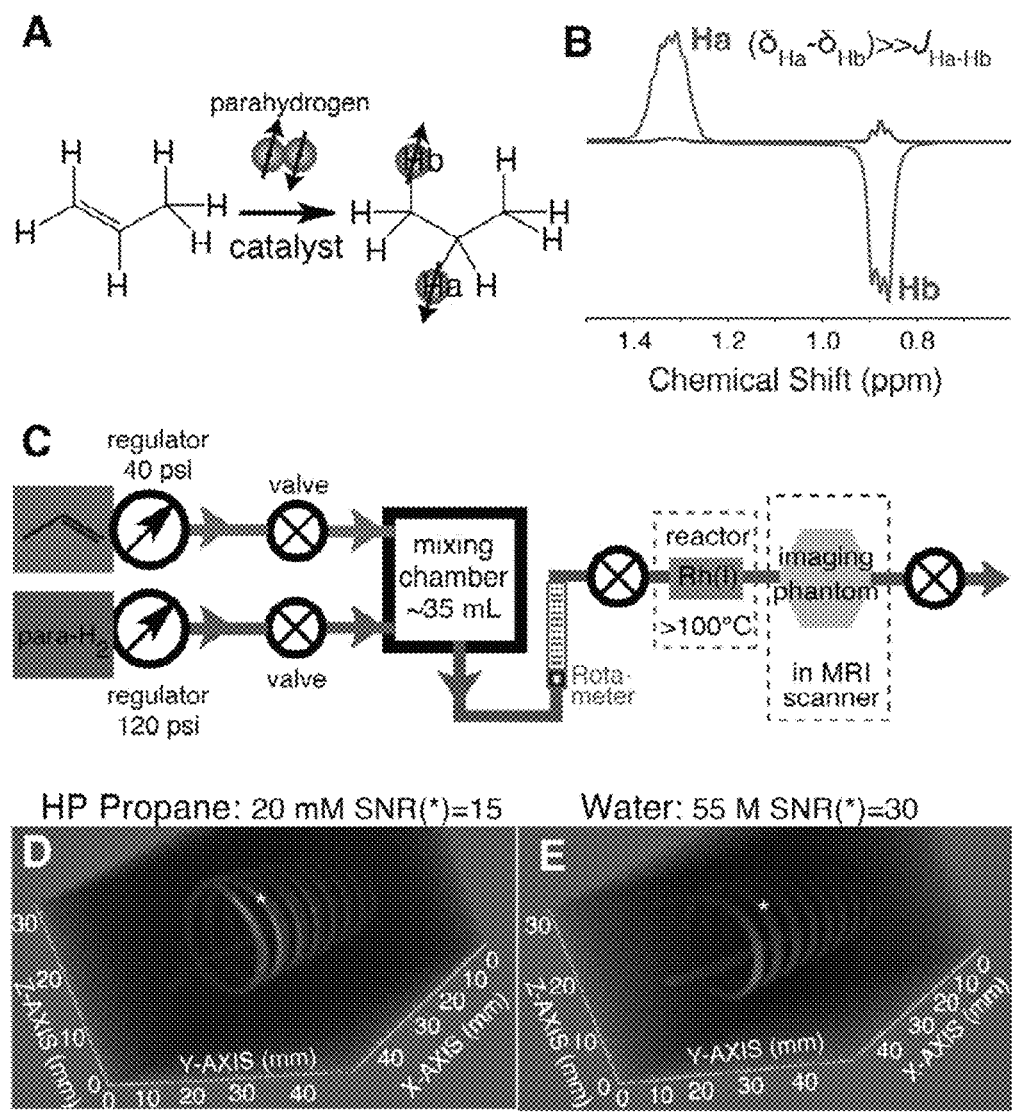
FIG. 1 shows preparation of hyperpolarized propane using spin order of parahydrogen and Adiabatic Longitudinal Transport After Dissociation Engenders Net Alignment (ALTADENA) hyperpolarization.

Reference will now be made in detail to the embodiments of the present invention, examples of which are illustrated in the accompanying drawings.

The present invention proposes the use of low magnetic fields (e.g., 1-300 mT) to create singlet or pseudo-singlet states after a chemical reaction with parahydrogen to produce hyperpolarized gas. It can be used for low-field MRI of hyperpolarized propane gas, including the use of hyperpolarized propane for low-field MRI for ultra-fast (on a time scale of a second) molecular imaging of lung, brain, heart and other organs.

A chemical reaction of molecular addition of parahydrogen gas to unsaturated (C=C or C≡C bonds) molecular precursors has been shown to create pseudo-singlet states of nascent parahydrogen spins in the reaction product according to the following equation:

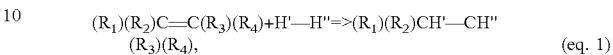

(eq. 1)

where H'—H" is parahydrogen molecule containing a pair of two proton nuclear spins in a pseudo-singlet state. These reactions have been shown for propylene to propane conversion by a specialized catalyst:

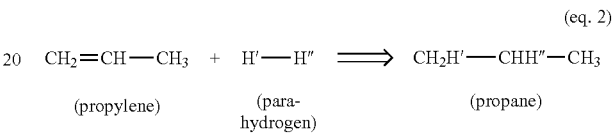

(eq. 2)

As long as the reaction undergoes the molecular mechanism, and the resulting product carries the parahydrogen pair with broken symmetry (e.g., in methyl and methylene groups shown above in eq. 2), the resulting transformed pseudo-singlet state can be observed in high magnetic fields using Adiabatic Longitudinal Transport After Dissociation Engenders Net Alignment (ALTADENA) experiment. The transformed pseudo-singlet state of these proton nuclear spins can be detected as a significantly enhanced nuclear magnetic resonance (NMR) signal by several orders of magnitude (compared to equilibrium NMR signal). This enhanced NMR signal is also typically referred to as hyperpolarized NMR signal or hyperpolarized NMR state.

Unfortunately, the hyperpolarized states are metastable in general and decay exponentially back to equilibrium nuclear spin polarization according to relaxation time $T_1$. The $T_1$ relaxation process is very efficient for propane with $T_1$<1 s at high magnetic fields, e.g., several Tesla magnetic fields of conventional MRI scanners and high-resolution NMR spectrometers. Such short $T_1$ is too short for any meaningful biomedical use, e.g., inhalation following by in vivo ultra-fast (on the time scale of a second) MRI.

The inventors propose preparation of significantly longer-lived hyperpolarized state of propane by performing the above reaction (eq. 2) in low magnetic field (e.g., Earth magnetic field or similar), and keeping the produced hyperpolarized (HP) propane in low magnetic fields under condition of $|δ(H')-δ(H")|<J(H'—H")$, where $δ(H')$ and $δ(H")$ are the chemical shifts of H' and H" nuclear spins in hyperpolarized propane (eq. 2) (and $|δ(H')-δ(H")|$ is an absolute value of the difference between the chemical shifts (of H' and H" in hyperpolarized propane) expressed in units of Hz), and $J(H'—H")$ is the spin-spin coupling between H' and H" nuclear spins.

With $J(H'—H")$ of ~5-10 Hz for three-bond spin-spin coupling, and chemical shift difference on the order of 0.5 ppm (parts per million), this effect is restricted to magnetic fields on the order of ~0.3 T and below, i.e., the regime usually referred to as low-field MRI. As long as the above condition is fulfilled, the two hyperpolarized spins in hyperpolarized propane maintain pseudo-singlet state (zero and low magnetic fields) with significantly longer (exponential) relaxation time $T_S$ nearly an order of magnitude greater (e.g., ~5 s) than the corresponding high-field $T_1$. The significantly prolonged lifetime of hyperpolarized state can therefore be used for biomedical application, e.g., inhalation following by MRI of hyperpolarized propane gas.

True singlet states are typically NMR invisible, e.g., no NMR or MRI signal is seen after radio-frequency (RF) excitation of nuclear spins. As a result, the elongated lifetime hyperpolarized propane by the above method using low magnetic fields are not useful using conventional MRI and NMR detection and nuclear spin preparation. However, the spin order of pseudo-singlet states of propane is converted into observable magnetization using specialized NMR radio-frequency sequences.

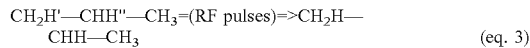
(eq. 3)

where H on the right side of eq. 3 denotes conventional nuclear spin magnetization, which is NMR and MRI observable and can be used for NMR spectroscopy and ultra-fast MRI imaging. While the $T_1$ relaxation of this observable magnetization is very efficient, sub-second (or on the time scale of ~1 second) MRI can image hyperpolarized propane. The produced in vivo images can include images of lungs after inhalation as well as other organs, after $CH_2H'$—$CHH''$—$CH_3$ transport including (but not limited to) brain, blood, heart.

Overpopulated pseudo-singlet state of propane can be prepared by many methods including Dynamic Nuclear Polarization (DNP) and Parahydrogen Induced Polarization (PHIP), as shown above. Nevertheless, it is the low magnetic field that creates the long-lived nature of overpopulated singlet or pseudo-singlet states of propane and possibly other similar molecules.

Short life-time of hyperpolarized propanes (including variants of propane with isotopic labels such as deuterium, $^{13}C$ and others) and other gaseous agents are significantly extended (by ~order of magnitude or potentially more). Conventional proton MRI can be used for hyperpolarized imaging reporting on functional information about lungs, brain and other organs.

Hyperpolarization increases the sensitivity of Magnetic Resonance by 4-6 orders of magnitude (1). This increase in sensitivity enables the detection of dilute exogenous contrast media at low in vivo concentrations. The delivery of hyperpolarized (HP) contrast media by inhalation for functional and molecular imaging is particularly attractive, because of its convenience and relative non-invasiveness.

To date, $^3He$, $^{129}Xe$, $^{83}Kr$ and other noble gases (2) were successfully hyperpolarized by Spin Exchange Optical Pumping (SEOP) method (3), and $^3He$ and $^{129}Xe$ (4) were successfully implemented in clinical trials. HP $^3He$ is the most sensitive noble gas, because of its favorable nuclear spin properties, e.g., gyromagnetic ratio $\gamma_{3HE}$ of 0.76 is that of proton. However, due to its limited quantities arising from tritium decay of nuclear weapons, very high cost, and mandatory allocations for US Department of Homeland Security, it is unlikely to see a widespread biomedical use. The next most promising noble gas is $^{129}Xe$, which can be polarized to the order unity on a clinical scale (5), has relatively high $\gamma_{129XE} \sim 0.28 \times \gamma_H$, and relatively long in vivo gas-phase life time, i.e., $^{129}Xe$ $T_1 \sim 20$ s (4). Despite being very promising imaging modalities capable for measuring lung function (4), probing brain function and others, HP $^{129}Xe$ technology has several major challenges for a widespread clinical translation: (i) natural abundance is only ~26% and isotopic enrichments is frequently needed to maximize the payload of this contrast agent, (ii) advanced high-cost SEOP hyperpolarization equipment (frequently called hyperpolarizer) is required to produce relatively small quantities (~1~20 L/h) of HP agents, (iii) a custom MRI scanner with multi-nuclear capability and special radio-frequency (RF) coils is required for $^{129}Xe$ imaging (4). The latter factor in particular made this technology available only to a few premier sites in the world.

A potential HP alternative to obviate the shortcomings of HP $^{129}Xe$ (and other noble gases) technology is the use of proton hyperpolarized contrast agent, which can be universally imaged using conventional MRI scanners. While direct hyperpolarization of gaseous contrast agents is indeed feasible and have been demonstrated, very short relaxation time $T_1$ of <1 s depolarizes the produced HP state significantly faster compared to its handling and inhalation time, which requires several seconds.

FIG. 1 demonstrates preparation of HP propane using spin order of parahydrogen and Adiabatic Longitudinal Transport After Dissociation Engenders Net Alignment (ALTADENA) (6) hyperpolarization technique, which results in two hyperpolarized (methylene and methyl) protons per each propane molecule. In this procedure, the pseudo-singlet state is first prepared at very low (e.g., Earth field) magnetic fields. This pseudo-singlet state is dissociated by adiabatic transfer to high magnetic field, which enables the detection of significantly enhanced emissive (Ha, FIG. 1, part (B)) and absorptive (Hb, FIG. 1, part (B)) NMR signals, because the difference in chemical shifts of two nascent protons is significantly greater than their spin-spin coupling, i.e., $\delta_{Ha}-\delta_{Hb} >> J_{Ha-Hb}$ Despite efficient $T_1$ relaxation ($T_1(CH_2)$=532±6 ms and $T_1(CH_3)$=616±16 ms at 9.4 T) this ~1% HP contrast agent can be imaged under conditions of constant flow (7), where the depolarized gas is quickly replaced by the freshly produced agent. FIG. 1, part (D) demonstrates an example of true 3D MRI with very high spatial (0.5×0.5×0.5 $mm^3$ voxel size) and temporal (21.4 s-long scan) with sensitivity approaching to that of water, FIG. 1, part (E).

FIG. 1 shows NMR spectroscopy and MRI imaging of ALTADENA HP propane in continuous flow. Part (A) shows a reaction scheme of molecular addition of parahydrogen to propene resulting in HP propane, Part (B) shows a high-resolution ALTADENA NMR spectroscopy of hyperpolarized propane gas in continuous flow at 9.4 T, Part (C) shows a schematic of ALTADENA experimental setup for HP propane detection at 4.7 T MRI and 9.4 T NMR, Part (D) shows a 3D gradient echo (GRE) imaging of HP propane in continuous flow at 4.7 T, Part (E) shows corresponding image of still water. Both images were acquired with 0.5×0.5×0.5 $mm^3$ spatial voxel resolution in 21.4 s.

A potential solution to extend the lifetime of HP propane is the use of non-dissociated pseudo-singlet states, which can significantly increase the relaxation times (as much as orders of magnitude) (8). A pseudo-singlet state of propane is created by the use of low magnetic field of 0.0475 T, which is ~100 times lower than 4.7 T field of MRI scanner used for HP propane imaging shown in FIG. 1, part (D), and ~30 times lower than the field of 1.5 T clinical MRI scanner. The experimental setup shown in FIG. 1, part (C) was used in the stopped-flow regime for low-field NMR studies, where the HP propane gas was stopped inside ~2 mL cavity placed in 0.0475 T MRI scanner.

Figure 2:
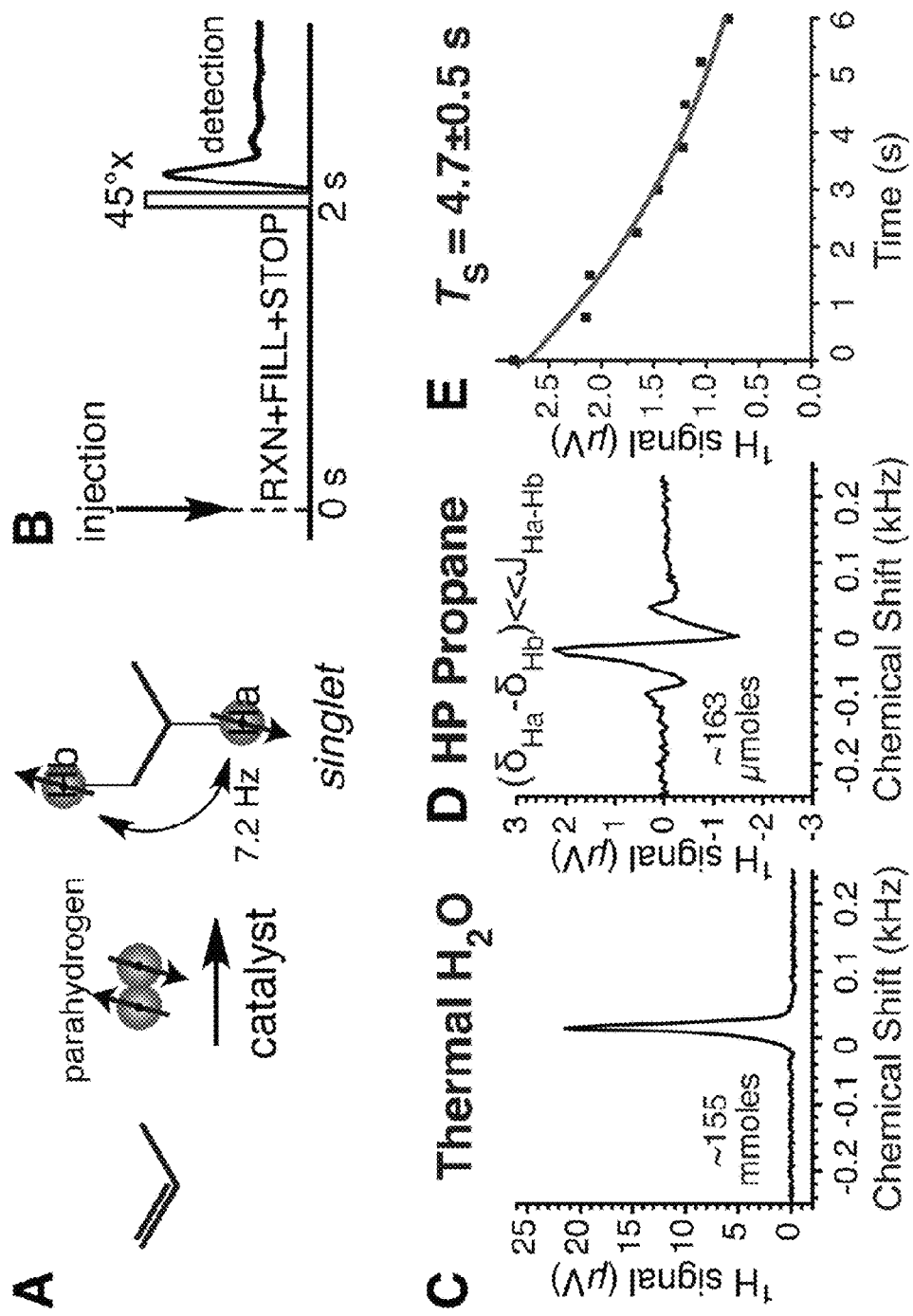
FIG. 2 shows low-field single-scan NMR spectroscopy at 0.0475 T.

The direct detection of NMR signal, FIG. 2, part (D), demonstrates very low NMR signal in one NMR line with relatively low SNR. While the directly observable signal was comparatively smaller than that from ~2.8 mL of water, FIG. 2, part (C), under equilibrium thermal polarization, this overpopulated pseudo-singlet state is significantly longer lived with $T_S$=4.7±0.5 s, which is nearly an order of magnitude increase compared to high-field $T_1$ of methyl and methylene protons.

The collapse of NMR lines resulting in reduced NMR sensitivity is a clear disadvantage of direct detection of such singlet state, although the increase in $T_S$ from ~0.6 s to 4.7 s is clearly attractive, because it is now sufficient for delivery and inhalation (2). For example, it is several fold greater than $T_1$ of HP [83]Kr in vivo of ~1-1.3 s, which is pursued as a potential in vivo contrast agent (2).

FIG. 2 shows Low-field single-scan NMR spectroscopy at 0.0475 T; Part (A) the diagram of molecular addition of parahydrogen gas to propene resulting in HP propane, Part (B) shows the sequence of events, Part (C) shows a single-scan reference spectrum of 2.8 mL water acquired with 45° excitation RF pulse, Part (D) shows single-scan reference spectrum of HP propane (via ALTADENA) obtained using protocol depicted in display (B) and the same acquisition parameters as in display (C), Part (E) shows $T_S$ decay of overpopulated propane pseudo-singlet state monitored by 7° excitation RF pulse every 0.75 seconds.

A number of RF pulse-sequences were recently developed for transformation of NMR hyperpolarization stored in the pseudo-singlet state into observable nuclear magnetization (9-11). Here, Spin-Lock Induced Crossing (SLIC) based RF pulse sequence was employed to convert the prepared ALTADENA based pseudo-singlet state into observable magnetization, see FIG. 3. A significantly greater NMR signal was detected in FIG. 3, part (D) compared to that in FIG. 2, part (D). The enhancement of nuclear spin polarization $\epsilon$ was >10,000 corresponding to absolute nuclear spin polarization % $P_H$>0.16% per each proton. The lower limit polarization enhancement is an estimate based on assumption of 100% reaction yield, FIG. 1, part (A). A spectrum of thermally polarized water with ~$10^3$ greater molar quantity, FIG. 2, part (C), was used for signal referencing purposes, because recording of propane thermal NMR spectrum would require ~$10^8$ signal averages, which is impractical (>10 years).

The detected % $P_H$ is notably reduced compared to % $P_H$~1% observed in high-field studies, FIG. 2, part (D). The decrease in apparent nuclear spin polarization is in part (d) due to relaxation during ~2 s-long $B_1$ spin-lock and other relaxation processes. Furthermore, the SLIC procedure was not fully optimized and performed under conditions of very low power decoupling, which is challenging, because of non-linearity and high noise figure of high-power RF amplifiers in μW regime. While the relaxation losses are difficult to avoid, the choice of power-optimized RF hardware and further RF pulse sequence optimization can potentially minimize hyperpolarization losses.

Figure 3:
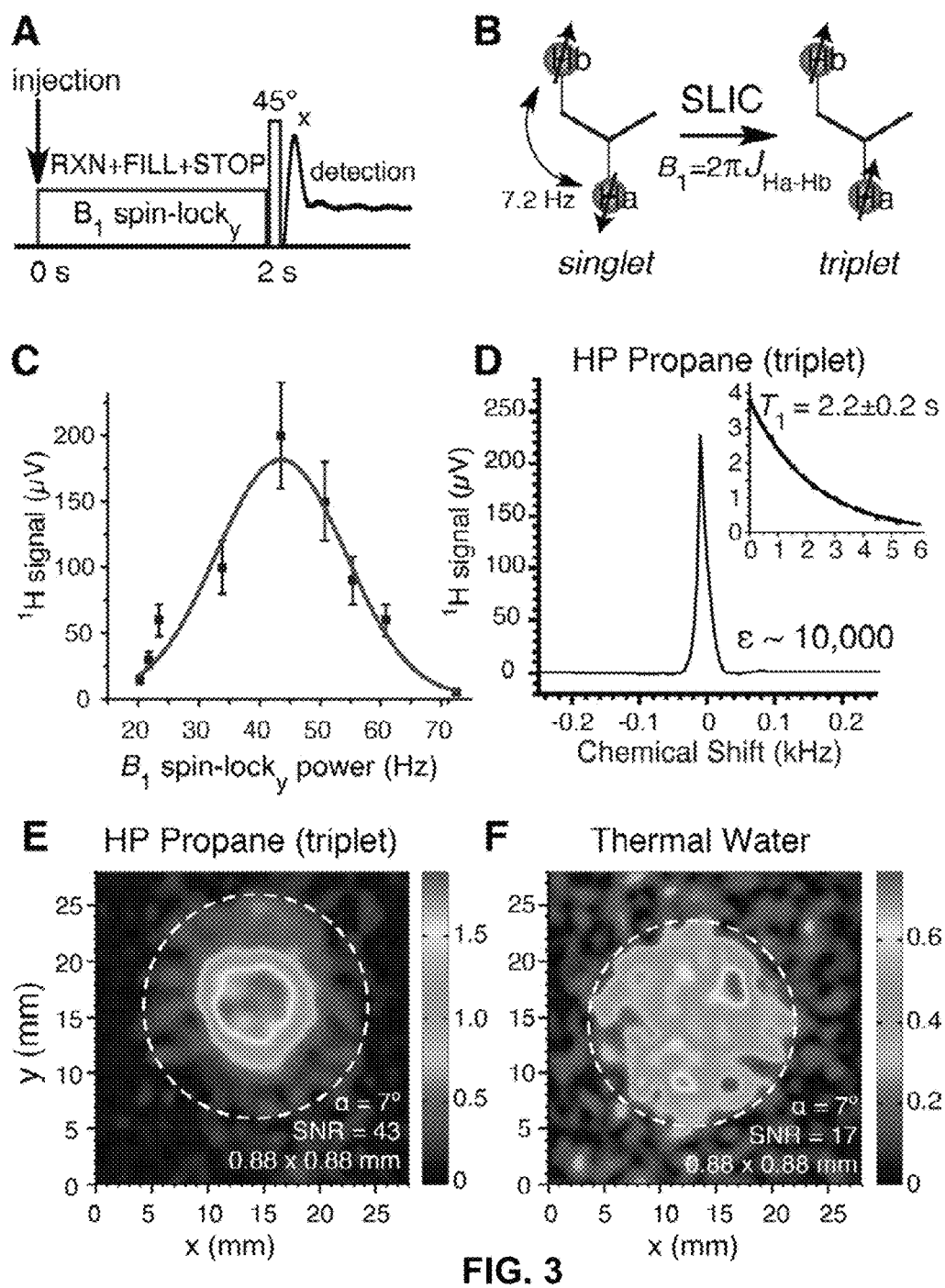
FIG. 3 shows NMR studies of ALTADENA HP propane irradiated with continuous wave (CW) decoupling at 2.0 MHz.

This produced HP triplet magnetization obeys a different relaxation rate of $T_1$=2.2±0.2 s, which is shorter than $T_S$, but sufficiently long for fast imaging. Proof-of-principle sub-second MRI with HP propane in triplet state is shown in FIG. 3, part (E) and a corresponding image of thermally polarized water is presented in FIG. 3, part (F). These images were acquired at 0.0475 T using MRI RF coil (12) with ~40% sensitivity of 4.7 T MRI coils such as that used for MRI presented in FIG. 1, part (D). In principle, the sensitivity of low-field MRI can surpass high-field MRI sensitivity for detection of hyperpolarized contrast agents including HP propane studied here (12).

FIG. 3 shows NMR studies of ALTADENA HP propane irradiated with continuous wave (CW) decoupling at 2.0 MHz ($B_0$=0.0475 T). Part (A) shows a sequence of events including SLIC block of $B_1$ spin-lock; Part (B) shows $^1$H spectrum detected using the sequence described above (inset) $T_1$ decay of produced triplet-state hyperpolarization; Part (C) shows schematic of propane pseudo-singlet state conversion to a triplet state via SLIC pulse-sequence block, Part (D) shows $^1$H signal dependence on the applied $B_1$ spin-lock power.

Note that the produced signal is at maximum at an estimated $B_1$=44 Hz using 36 μW of RF power, which is in qualitative agreement with $2\pi_{Ha-Hb}$ where $J_{Ha-Hb}$=7.2 Hz, Part (E) shows projection gradient echo (GRE) imaging of HP propane in triplet state using the following imaging parameters: TE/TR=7.0/20 ms, acquisition time=6.4 ms, spectral width (SW)=5.0 kHz, RF excitation pulse ($\alpha$)=7° (6.0 μs), field of view (FOV)=28×28 mm$^2$ using 32×32 imaging matrix with 2 dummy scans with total imaging time of ~0.7 s. An estimated % $P_H$ was ~0.08% at the beginning of imaging sequence. The disc (dotted circle) highlights the wider (but thinner) section of the 2 mL phantom. Part (F) A corresponding image of thermally polarized water. Dotted circle identifies the 1.75 cm-diameter of 2.8 mL sphere of water. No compressed sensing was used, and signal-to-noise ratio (SNR) of the maximum voxel SNR was 43 in (E) and 17 in (F) respectively.

Quality (speed, SNR and spatial resolution) of GRE images presented in FIG. 1, part (D) and FIG. 3, part (E), should not be compared directly, because image presented in FIG. 1, part (D) is enhanced by (i) RF excitation pulses with significantly greater flip angle, (ii) 192 times more encoding steps, (iii) more sensitive RF coil, and (iv) flowing gas constantly replenishing polarization of propane gas being imaged. Nevertheless, 0.88×0.88 mm$^2$ in-plane spatial resolution have been demonstrated in ~0.7 s total acquisition time, which was largely limited by electronics response time. 3D MRI on a time scale of seconds of HP propane is feasible using 3.48 ms repetition time (FIG. 2, part (D)) and compressed sensing image encoding, which has been already shown to accelerate HP MRI by 3-4 fold and can potentially achieve more than an order magnitude increase in temporal resolution. Furthermore, ultra-fast (<5 s) 3D MRI of patient lungs on a single breath-hold with HP has been demonstrated with <25% hyperpolarized [129]Xe without compressed sensing (5).

HP propane and potentially other gaseous HP $^1$H contrast agents offer multiple significant advantages over HP noble gases and other HP heteronuclear contrast agents (13) even under conditions of nominally lower hyperpolarization levels. First, each HP propane molecule carries a double payload of hyperpolarization compared to monoatomic HP [129]Xe, [3]He, [83]Kr and others. Second, protons have the highest nuclear gyromagnetic ratio $\gamma_H$. For example, $\gamma_H$ is 3.6 times greater than 7129XE. Third, proton spins have nearly 100% natural abundance, while [129]Xe natural abundance is 26%, and much worse for [3]He and [83]Kr. For example, these compounding factors make [129]Xe detection more than 27 times less sensitive than $^1$H detection. There are other practical challenges of low-$\gamma$ nuclei detection: (i) the requirement of specialized and costly hardware is required, which is not universally available, and (ii) significantly higher gradient power (proportional to the square of the ratio of gyromagnetic ratios of proton and low-$\gamma$ nucleus) requirements (13) and (iii) contrast agent cost. The above advantages make this low-cost HP propane a very promising contrast agent for biomedical use.

Propane is a non-toxic asphyxiant, and it has been shown to be non-toxic and safe in a long-term (90-day long) occupational exposure study at the concentration up to 10,000 ppm, which is below its lower explosive level (LEL)

of 2.1% (14). Moreover, ALTADENA hyperpolarization is a relatively simple instrumentation-non-demanding method requiring only parahydrogen, propene and a special solid-phase heterogeneous catalyst. Delivery and inhalation of ALTADENA HP propane would require several seconds rendering the potential biomedical use feasible due to lengthened relaxation time $T_S$ vs. significantly shorter $T_1$. The transformation of pseudo-singlet to a triplet state was achieved with 36 μW of RF power on a small animal scale, and scaling to a human subject will likely require less than a Watt of RF power with negligible specific absorption rate (SAR) at low resonance frequencies (15) making it a safe procedure.

While the catalyst performs efficient hydrogenation of parahydrogen gas to propene, FIG. 1, part (A), the molecular addition pathway likely represents only a small fraction (a few percent) of overall hydrogenation yield. Improving the yield of heterogeneous hydrogenation, handling of HP propane, and MR singlet transformation and imaging sequences can potentially further improve the detection MRI sensitivity of HP propane by 1-3 orders of magnitude enabling sensitive high-resolution MRI of lungs and other applications with sub-second temporal resolution.

Deuteration of molecular propene precursor results in only a small increase in $T_1$ values of the HP product as demonstrated here by high-field NMR and MRI, and thus provides little benefit in prolonging the hyperpolarization lifetime for conventional high-field (1 T and above) MRI. However, the use of low magnetic fields allows the preparation of hyperpolarized long-lived spin states of the nascent pair of hydrogens of the parahydrogen after its pairwise addition to propene-$d_6$, and the significantly increased hyperpolarization lifetime is potentially suitable for biomedical imaging applications, similarly to that described above for PHIP hyperpolarized propane.

Figure 4:
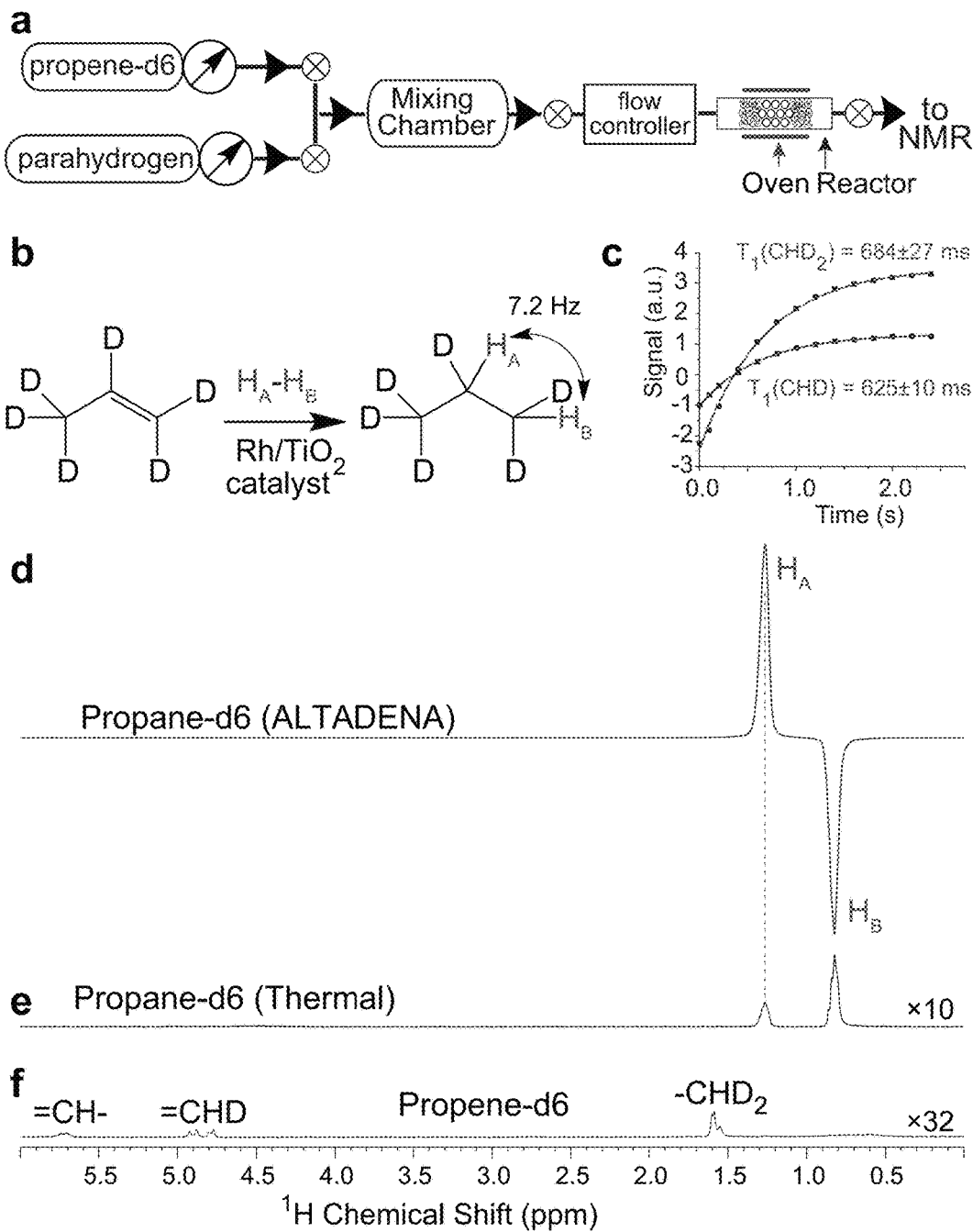
FIG. 4 shows preparation of hyperpolarized propane-$d_6$ using spin order of parahydrogen and Adiabatic Longitudinal Transport After Dissociation Engenders Net Alignment (ALTADENA) hyperpolarization.

The conventional ALTADENA (6) experiment relies on the pairwise addition of parahydrogen to an unsaturated precursor in a very low magnetic field under conditions of $\gamma_H B_0(\delta(H_A)-\delta(H_B))/2\pi E \ll J_{HA-HB}$, which is followed by a rapid sample transfer to a high-field NMR spectrometer and detection of the dissociated singlet of nascent parahydrogen protons under conditions of $\gamma_H B_0(\delta(H_A)-\delta(H_B))/2\pi \gg J_{HA-HB}$, where $\gamma_H B_0(\delta(H_A)-\delta(H_B))/2\pi$ is the chemical shift difference (in units of Hz) of the two nascent protons $H_A$ and $H_B$, see FIG. 4, part (b). The resulting ALTADENA spectrum (FIG. 4, part (d)) of HP propane-$d_6$ shows the expected two NMR lines corresponding to $H_A$ and $H_B$ protons of propane-$d_6$ gas with the signal enhancement ϵ(app,flow)=100±5 (measured by comparison with thermal spectrum of stopped gas, FIG. 4e; the signal enhancement is similar to that observed for non-deuterated propane under similar experimental conditions as described above).

FIG. 4 shows ALTADENA single-scan NMR spectroscopy of HP propane-$d_6$ with detection at 9.4 T. Part a shows experimental setup diagram; part (b)) shows the diagram of pairwise addition of parahydrogen (shown as $H_A$-$H_B$) to propene-$d_6$ resulting in propane-$d_6$; part (c) shows $T_1$ measurements for thermally polarized propane-$d_6$ by inversion-recovery method (16) at 9.4 T; part (d) shows ALTADENA spectrum of HP propane-$d_6$ with ϵ(app,flow)=100±5 with respect to spectrum shown in FIG. 4, part (e) of stopped thermally polarized propane-$d_6$ gas, unequal thermal resonances for CHD and CD$_2$H protons are formed due to fast H-D exchange reaction over metal surface of heterogeneous catalyst, FIG. 4 part (f) shows 32-scan spectrum of thermally polarized propene-$d_6$ gas showing residual $^1$H proton signals in propene-$d_6$ groups.

While deuteration may increase $T_1$, this effect was found to be very minor at 9.4 T. For example, $T_1$ (CHD$_2$-) is 684±27 ms vs. $T_1$ (CH$_3$—)=616±16 ms, and $T_1$ (—CHD-) is 625±10 ms vs. $T_1$ (—CH$_2$—)=532±6 ms, in propane-$d_6$ and propane respectively. These relatively low $T_1$ values present an experimental challenge for the detection of HP gas because of the relaxation losses during gas transport from the reactor to the NMR detector, FIG. 4, part (a). Moreover, as indicated above short $T_1$ is a fundamental barrier for potential biomedical translation of HP propane (and other HP hydrocarbons) as an inhalable HP contrast agent for pulmonary imaging in a manner similar to HP $^{129}$Xe (4, 17) and other HP noble gases.

Despite the limitations associated with a relatively short $T_1$, HP propane-$d_6$ gas can be successfully used for high-resolution hyperpolarized imaging. An example of high-resolution 3D MRI is provided in FIG. 5, part (a), where a spiral-shaped phantom was filled with the flowing HP propane-$d_6$ gas. The MR image with 0.5×0.5×0.5 mm$^3$ spatial and 17.7 s temporal resolution is demonstrated using polarization levels of $P_H$~1% for HP propane-$d_6$ gas. A corresponding image of thermally polarized water is provided in FIG. 2b. The SNR of 3D images of HP propane-$d_6$ gas and water were similar, demonstrating that proton images of hyperpolarized gases can be obtained with a quality similar to that of water.

The clear advantages of proton hyperpolarized gas (vs. $^{129}$Xe (4, 5, 17) or other hyperpolarized noble gases) such as propane-$d_6$ shown here include the use of widely available proton-detecting imaging hardware and conventional and advanced (18) fast 3D proton MRI sequences. For example, the images presented in FIG. 5 part (a) were acquired using a conventional 3D GRE MRI sequence as supplied by the MRI instrument manufacturer. It should also be noted that the images presented in FIG. 5 part (a) have an approximately 2-fold better spatial resolution (as measured by the voxel size) compared to 0.625×0.625×0.625 mm$^3$ spatial resolution demonstrated earlier with HP non-deuterated propane (19).

Figure 5:
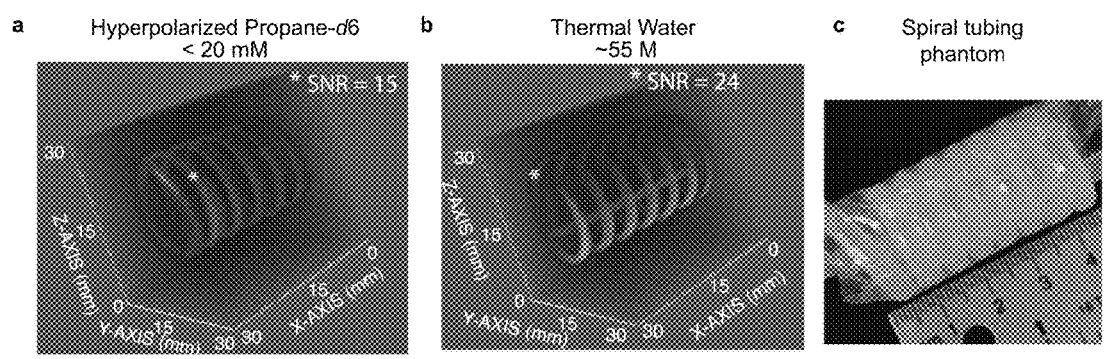
FIG. 5 shows high-resolution high-field MRI scan of flowing propane-$d_6$ gas and water reference scan.

FIG. 5 shows high-resolution 3D gradient echo (GRE) MRI at 4.7 T. Part a shows 3D MRI of flowing ~20 mM HP propane gas with 0.5×0.5×0.5 mm$^3$ spatial and 17.7 s temporal resolution with 32×32×32 mm$^3$ field of view. Part b) shows the corresponding image of still thermally polarized 55 M tap water, and part (c)) shows the photograph of spiral phantom used for MRI imaging studies shown in FIG. 5 parts a and b. Signal-to-noise ratio (SNR) values are provided for representative voxels marked with white asterisk (*).

Furthermore, NMR and MRI detection of HP propane-$d_6$ can be performed at low magnetic fields (20-22). In addition, the detection efficiency of HP NMR and MRI (defined as SNR) in low magnetic fields can in fact significantly exceed that of high-field HP detection (12, 23, 24). Low-field NMR can offer the regime of a strongly coupled spin system with $\gamma_H B_0(\delta(H_A)-\delta(H_B))/2\pi < J_{HA-HB}$ and therefore the singlet spin state of the nascent protons derived from parahydrogen may remain partially associated. NMR detection of HP propane-$d_6$ obtained using the setup shown in FIG. 6a enabled NMR detection at 0.0475 T (23, 24), where $\gamma_H B_0(\delta(H_A)-\delta(H_B))/2\pi$ of ~1 Hz is significantly smaller than $J_{HA-HAB}$ of ~7 Hz. The spectroscopic NMR detection of stopped HP propane-$d_6$ gas (FIG. 6b) revealed a strongly enhanced signal with ϵ(app, stopped)~6000 corresponding to $P_H$~0.1% (per nascent proton) by referencing to the NMR signal of thermally polarized water. Experimentations with non-deuterated HP propane under identical experimental conditions (FIG. 6 part (b)) revealed a significant collapse of the NMR signal due to a small chemical shift difference between $H_A$ and $H_B$.

Figure 6:
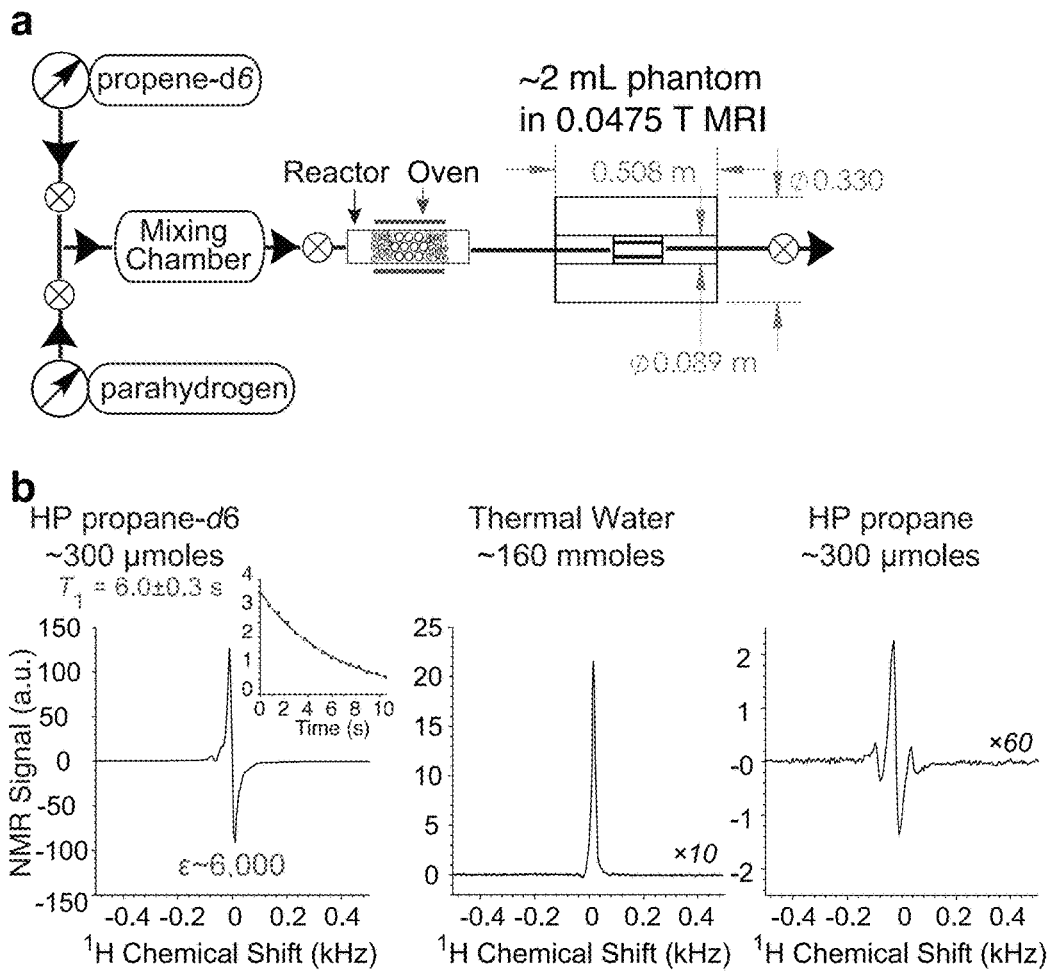
FIG. 6 shows experimental NMR spectroscopic studies of stopped-flow hyperpolarized propane-$d_6$ gas at 0.0475 T.

FIG. 6 shows stopped-flow NMR spectroscopy of hyperpolarized propane-$d_6$ gas at 0.0475 T. FIG. 6 part (a) shows an experimental setup diagram. The left display of FIG. 6 part (b) shows single-scan NMR spectrum of HP propane-$d_6$ after pairwise addition of parahydrogen to propene-$d_6$ in Earth magnetic field; the inset shows the decay of HP signal measured with a small-angle RF excitation pulse ($\alpha=7°$). The middle display of FIG. 6 part (b) corresponding spectrum of thermally polarized water; the right display of FIG. 6 part (b) shows the corresponding spectrum of HP propane. It should be noted that the effect of 7° RF excitation pulse on magnetization is negligible (>99% of residual polarization is retained after each RF pulse) conveniently allowing in situ direct monitoring of exponential signal decay, i.e. $T_1$ measurement (5, 23, 25).

Figure 7:
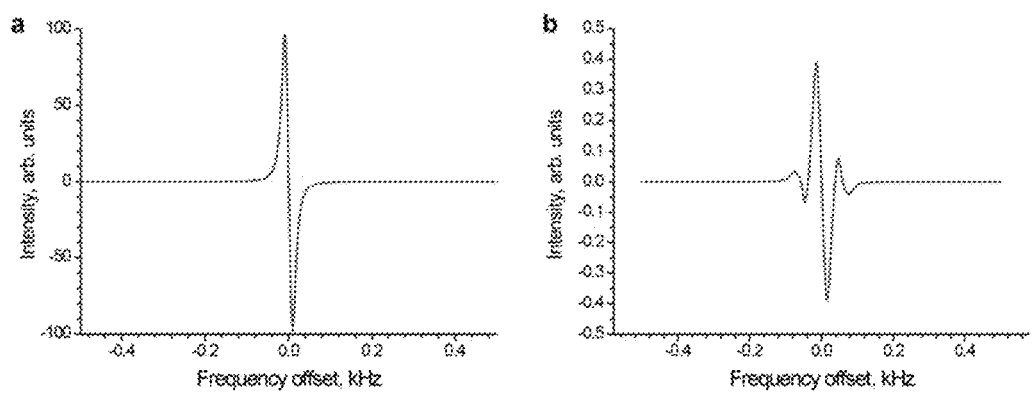
FIG. 7 shows theoretically simulated NMR spectroscopic studies of stopped-flow hyperpolarized propane-$d_6$ gas at 0.0475 T.

Theoretical simulations of the experiments intended to verify the observed significant difference in the NMR signals of deuterated and non-deuterated propane were performed, FIG. 7, graph (a) and graph (b), respectively. The very large difference between signal enhancements for propane and propane-$d_6$ can be rationalized as follows. At the magnetic field of 0.0475 T, the methyl and methylene proton spins of propane are strongly coupled and essentially represent a system of 8 almost magnetically equivalent spins. In the reaction of propene with parahydrogen, the numerous spin states of propane are populated in such a way that the allowed NMR transitions correspond to very small spin level population differences and thus give very weak signals, whereas significant population differences created by the reaction correspond to transitions which are normally forbidden.

In terms of a two-spin system, this would correspond to small population differences within the manifold of the NMR-active triplet spin state, and a large population difference between the singlet and triplet manifolds which gives no observable NMR signal. However, because the two chemical shifts are unequal, mixing of the triplet and singlet states makes the nominally forbidden transitions slightly allowed, which, combined with the large population difference between the singlet and triplet manifolds leads to the observation of a moderate intensity spectrum. We note that for an 8-spin system, this "singlet-triplet" terminology is applicable only in qualitative terms, but it is still quite illustrative. For propane-$d_6$, the presence of deuterium atoms removes the near-magnetic-equivalence of the two H atoms inherited by propane from parahydrogen, and the corresponding mixing of spin states ensures that large populations differences are now associated with fully allowed transitions, leading to much larger signal intensity in the observed NMR spectrum (see FIG. 7, graph (a) corresponding to propane-$d_6$ and FIG. 7, graph (b) corresponding to non-deuterated propane respectively).

The polarization decay time measurements for HP propane-$d_6$ yielded a value of $T_{1,eff}=6.0\pm0.3$ s (FIG. 6 part (b) inset), which is an order of magnitude greater than the high-field $T_1$ value of ~0.6 s. Furthermore, the addition of 0.2 atm of $O_2$ introduced to HP propane-$d_6$ did not affect its $T_{1,eff}$ of ~6 s. The increase in $T_1$ (and its insensitivity to paramagnetic $O_2$ impurity) is highly desirable, because it renders the opportunity to use HP propane gas for biomedical applications as a potential inhalable proton hyperpolarized contrast agent.

This effect of creation of longer-lived large population differences between the spin states of nascent parahydrogen proton spins is likely to be universal for PHIP (and potentially other HP methods), and we term it Nuclear Alignment of Spin Hyperpolarization via Interactions in Long-lived Low-field Ensembles (NASHVILLE) to make distinction with PASADENA and ALTADENA conditions. A number of perdeuterated PHIP precursors similar to propene-$d_6$ employed here are already available for efficient, i.e. resulting in near unity, hyperpolarization. These precursors can be used for PHIP of HEP for MRI angiography (26), TFPP for coronary plaque imaging (27), succinate (28, 29) for cancer imaging (30), phospholactate (31, 32) and propargylcholine (33).

FIG. 6 shows the calculated $^1H$ NMR spectra of HP propane and its isotopomers after pairwise addition of parahydrogen to corresponding propenes in a chemical reaction performed at 0.0475 T magnetic field. FIG. 6 part (a) shows the spectrum calculated for propane-$d_6$. FIG. 6 part (b) shows the weighted sum of the spectra of propane and [3-$^{13}C$]-propane (it is assumed that the two hydrogen atoms inherited from parahydrogen are in positions 1 and 2 in the propane molecule). The contribution of [3-$^{13}C$]-propane was multiplied by 0.011 to take into account $^{13}C$ natural abundance. Note the different vertical scales for the two spectra.

The increase of the lifetime of HP state of propane-$d_6$ at low magnetic field through creation of long-lived states is hardly surprising, because a significant increase in singlet lifetime vs. conventional $T_1$ was demonstrated in seminal works by Levitt (8, 9), Warren (10, 34), and others (35). While $T_1$ of HP propane-$d_6$ (~6 s) is relatively low, it exceeds that of HP $^{83}Kr$ (36), and it is certainly sufficiently long to enable in vivo administration via inhalation. However, we point out that it is the use of low magnetic field that enables preserving this long-lived states, which is the key innovation described.

Figure 8:
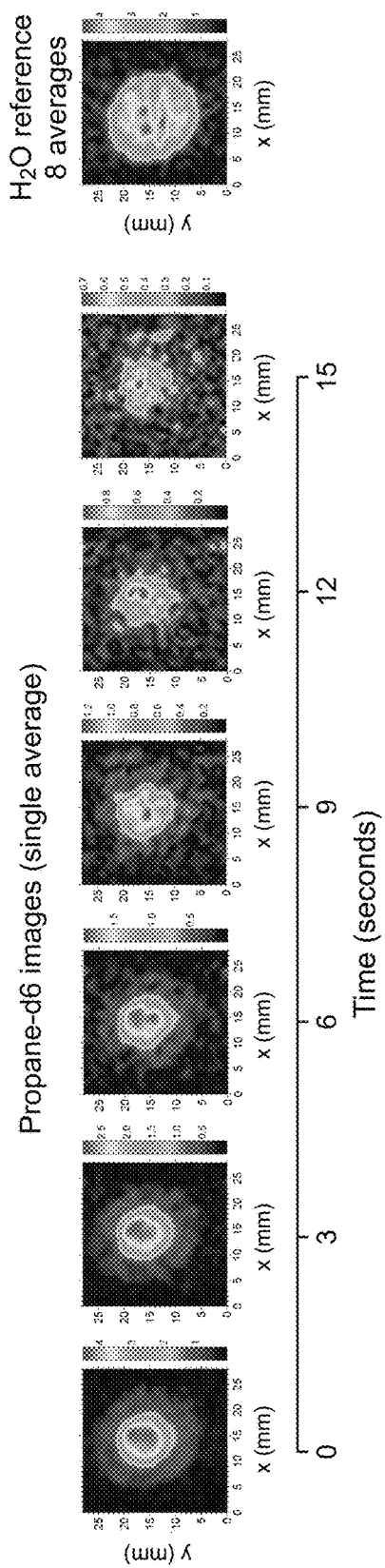
FIG. 8 shows experimental MRI imaging studies of stopped-flow hyperpolarized propane-$d_6$ gas at 0.0475 T.

Low-field MRI has a potential for biomedical application of HP propane-$d_6$ described above, and the feasibility of sub-second low-field MRI is successfully demonstrated in FIG. 8. 2D (without slice selection) GRE MRI images were acquired with sub-millimeter (0.88×0.88 mm² pixel size) spatial resolution in ~0.7 s. The repetition time (TR=20 ms) was limited by the electronics response, and can be significantly accelerated in the future similarly to the GRE MRI (TR=4.3 ms) presented in FIG. 5 part (a). Furthermore, shorter TR can also potentially enable sufficiently high scan speed required for 3D imaging of HP gas (5, 37).

The level of signal enhancement ($\epsilon$~6000) enabled higher SNR in the images of HP propane compared to that of thermally polarized water, see FIG. 8. This is important, because potential in vivo direct proton imaging of this HP contrast agent will have to consider the background signal from water in the surrounding tissue (38, 39). Moreover, the available $P_H$ was only 0.1% at 0.0475 T. Further improvements to achieve higher $P_H$ values are possible for boosting the imaging SNR, which would improve the dominance of the HP propane-$d_6$ signal over the thermal water background.

A significant discrepancy between the apparent $P_H$ values for HP propane-$d_6$ at high and low magnetic fields (~1% and 0.1%, respectively) can be explained by (i) the difference in experimental setup (experiments at high field utilized constant gas flow, whereas low-field experiments lacked flow control), (ii) additional relaxation losses in low-field experiments, because HP gas was stopped first, causing an additional time delay (~2-3 s). Moreover, partial collapse of an anti-phase NMR peak due to $B_0$ field inhomogeneities cannot be completely ruled out (40). Furthermore, the possibility of incorporation of more than one pair of parahydrogen into the final product via pairwise route cannot be ruled out.

HP propane-$d_6$ gas was prepared within seconds via heterogeneous catalytic hydrogenation. While a relatively small production quantity (a few mL) of HP propane-$d_6$ was demonstrated, there are no fundamental barriers for scaling it up to a clinically relevant dose of ~1 L. Despite a relatively low percentage polarization (0.1-1%) achieved for propane to date (19), it should be pointed out that each HP propane molecule carries a payload of two hyperpolarized protons compared to monoatomic hyperpolarized $^{129}$Xe. Furthermore, protons have a ~3.6-fold greater gyromagnetic ratio and a ~4-fold greater natural abundance compared to those of $^{129}$Xe. The combination (calculated as a product) of these factors makes HP propane ~40 times more sensitive compared to $^{129}$Xe at the same polarization level. Furthermore, the process of SEOP of noble gases is time consuming, whereas HP propane-$d_6$ can be prepared on demand, which can additionally enable signal averaging to improve SNR through potentially multiple inhalations of HP propane-$d_6$. Nevertheless, the recent technological (25, 41-44) and fundamental (5, 45) advances (46) in SEOP hyperpolarization of $^{129}$Xe, enabled $^{129}$Xe polarization to approach order unity (i.e. →100%). Therefore, despite nominally better detection sensitivity of propane vs. $^{129}$Xe, further improvements in hyperpolarization level of HP propane are required to truly enable better detection sensitivity of HP propane-$d_6$ vs. HP $^{129}$Xe in addition to the other two realized benefits of (i) direct proton detection enabling MRI imaging on widely available proton MRI scanners, and (ii) and the relatively ease of and cost (of hyperpolarization equipment) HP propane-$d_6$ production.

FIG. 8 shows sub-second single-average non-slice-selective 2D MRI of 150 mM HP propane-$d_6$ (~2 mL volume) at 0.0475 T with 0.88×0.88 mm$^2$ spatial and ~0.7 s temporal resolution with 28×28 mm$^2$ field of view. The same batch of HP propane was used for subsequent 2D MRI scans every 3 s. Note that propane-$d_6$ images are more intense in the center due to greater sample depth in the center of the phantom variable cylindrical shape. The image on the right shows the corresponding 2D image (8 averages) of 55 M thermally polarized water (~2.8 mL volume).

An additional benefit of HP propane-$d_6$ similarly to what is described above for non-deuterated HP propane is the use of proton NMR detection, which is universally available unlike detection of $^{129}$Xe, $^{13}$C and $^3$He requiring multinuclear detection capability (13). The main limitation of the described use of HP propane-$d_6$ at 0.0475 T is the prerequisite of low-field MRI scanners, which are less widespread than conventional high-field MRI scanners. However, it should be pointed out that low-field HP MRI (37, 47, 48) can be more sensitive than HP high-field MRI (12) making the low-field MRI a very well suited molecular imaging modality. Moreover, specific adsorption rate (SAR) is negligible at low resonance frequencies (15), which provides fewer limitations (for example, SAR can limit the speed of MRI scan) and an increased patient safety.

Propene-$d_6$ gas was efficiently hyperpolarized using HET-PHIP technique and Rh/TiO$_2$ catalyst allowing for preparation of pure HP propane-$d_6$ gas. While deuteration of propene precursor was not effective for increasing $T_1$ at 9.4 T, it nevertheless demonstrates a number of advantages compared to unlabeled propene. Low-field NMR at 0.0475 T enabled efficient direct detection of PHIP hyperpolarized propane-$d_6$ in contrast to non-deuterated PHIP polarized propane, i.e. without the requirement for complex polarization transfer sequences such as SLIC. The longer-lived low-field ensembles (NASHVILLE effect) additionally allow for a significant (factor of ~10) increase in hyperpolarization decay time. This new approach can potentially be extended to other perdeuterated precursors suitable for PHIP hyperpolarization. The feasibility of multi-scan low-field MRI was demonstrated with the spatial and temporal resolution of 0.88×0.88 mm$^2$ (pixel size) and ~0.7 s, respectively. Multiple sub-second MR images were recorded on a single batch of stopped-flow HP propane-$d_6$ gas during ~15 s-long time window. The feasibility of high-resolution MRI should pave the way to biomedical use of PHIP hyperpolarized propane-$d_6$ as an inhalable contrast agent for pulmonary imaging using proton MRI hardware and pulse sequences.

Ultra-high (>99.999%) purity $H_2$ gas was used to produce >90% para-state parahydrogen gas using parahydrogen generator described earlier (49). Propene (Sigma-Aldrich, p/n 295663) and propene-$d_6$ (99% atom D, Sigma-Aldrich 455687) were used as is. Supported metal nanoparticles (e.g., Rh on TiO$_2$) were used as a catalyst for molecular addition of parahydrogen to propene. Gases were mixed immediately before their use in a custom mixing chamber, which represented a previously described (23, 24) high-pressure ~60 mL polysulfone reactor filled with plastic balls to yield the effective chamber volume of ~30-60 mL. Propene-$d_6$ gas was filled in the chamber first, and the chamber was then filled with parahydrogen gas with ~9.5 bar total pressure and a 1:2 ratio of propene-$d_6$:parahydrogen gases. Note that when propene gas is completely hydrogenated, the resulting gas mixture consists of propane-$d_6$:parahydrogen in ~1:1 ratio. Rh/TiO$_2$ catalyst (1.6 nm particle size) was described earlier (19). Approximately 50 mg of this catalyst was packed inside an ⅛ in. OD copper tubing representing variable-temperature (VT) reaction chamber.

The hydrogenation reaction was performed in a temperature controlled reaction chamber at Earth magnetic field, and the resulting gas was transferred for detection to the 9.4 T NMR spectrometer via 1/16 in. OD (1/32 in. ID) Teflon tubing at a flow rate of 100 mL/min at 1 atm total gas pressure. HP gas was delivered to the bottom of a standard 5 mm NMR tube via 1/16 in. OD Teflon flexible tubing. The gas exited the NMR tube through an additional exhaust line (via 1/16 in. OD Teflon tubing) at the top of the NMR tube. For PASADENA experiments, a small quantity (a few mg) of Rh/TiO$_2$ catalyst was placed at the bottom of a standard 5 mm NMR tube, and the propene-$d_6$:parahydrogen mixture was delivered to the catalyst via 1/16 in. OD Teflon tubing. All experiments with hydrogenation at Earth magnetic field were conducted at reaction chamber temperature of ~100° C. While gas stream leaves the reactor being very hot, the gas cools down rather rapidly, because gases generally have relatively low thermal capacity, and because the gas passes through a significant section (>1 m long) of 1/16 in. ID tubing. As a result, when the material is transferred to the 9.4 T magnet, it is already equilibrated to room temperature. This was additionally checked by blowing the stream of produced gases over the hand of the experimenter, and the gas was found to be cooled. The apparent enhancement factor $\epsilon$(app,flow) was calculated by comparing the signal intensities of hyperpolarized (flow) and thermally polarized (stopped flow) gas samples using the method described earlier assuming that the HP gas already equilibrated to room temperature after passing though a very long section (>1 m) of tubing (19). The rapid gas cool-down is a convenient and advantageous feature of this method for potential biomedical translation.

High-field NMR spectroscopy study shown in FIG. 1, part (B) was performed at 9.4 T Bruker using high-resolution NMR spectrometer.

Varian 4.7 T preclinical MRI scanner was used for high-field MRI studies shown in FIG. 1, part (D) and FIG. 3, part (E). The experiments were conducted with a custom-built 38 mm ID dual-channel radio frequency (RF) coil, with the proton channel tuned to 200.25 MHz. All the experiments used the static magnetic field $B_0$ shim values obtained on a 10 mL sample of deionized water with half-height line width of ~3 Hz.

Both 4.7 T MRI (FIG. 1, part (D) and FIG. 1, part (E)) experiments' imaging sequence used Varian's version of a 3D gradient echo (GRE) sequence called ge3D with a total acquisition time (AQ) of 21.4 s and spectral width (SW) of 40 kHz. GRE excitation RF pulse had a Gaussian shaped with a pulse width of 500 μs for propane (15° at 76 mW) and water (2° at 1.3 mW) acquisitions. The repetition time (TR) for MRI experiments was between 3.48 ms, while TE was between 1.76 ms respectively. Isotropic imaging spatial resolution (voxel size) was 0.5×0.5×0.5 mm³ (125 nL) with 48×48×32 mm³ field of view (FOV) and 96×96×64 imaging matrix. No compressed sensing or image acceleration was employed.

For HP propane studies, 4.7 T MRI experiments were conducted using a spiral phantom constructed of Tygon™ (3/32 in. ID×3/16 in. OD, McMaster Carr, #5552K22) tubing, wrapped around plastic syringe to provide 3D structure for imaging studies. The phantom was longer than the imaging field of view (FOV) and was placed in the center of RF coil. For each hyperpolarized imaging experiment, propene (PHIP precursor) was mixed with parahydrogen in 1:2 molar ratio (40 psi propene and 80 psi parahydrogen) to yield a mixture of hyperpolarized propane and residual unreacted parahydrogen (~1:1 ratio) after passing it through over a solid supported metal nanoparticles (used as a catalyst for molecular addition of parahydrogen) placed inside 1/8 in. copper tubing heated to ~100° C. The propane was delivered into the spiral phantom (via 1/8 in. OD PTFE tubing with 1/16 in. ID) and released via the outlet (placed after the phantom) without any backpressure or additional flow restriction. Continuous flow rate (50-500 mL/min) of hyperpolarized propane/residual parahydrogen mix was maintained until the imaging acquisition was completed.

For propane-$d_6$ studies, high-field 3D MRI studies were conducted using a 4.7 T Varian MRI scanner (Varian, Palo Alton, Calif.) and a custom-built 38 mm ID dual-channel MRI coil tuned to $^1H$ frequency of 200.25 MHz. 3D gradient echo MRI sequence (ge3D) was used for MRI with the following parameters: spectral width (SW)=20 kHz, imaging matrix 64×64×64, field of view (FOV)=32×32×32 mm³, echo time (TE)=2.2 ms, repetition time (TR)=4.3 ms, voxel size 0.5×0.5×0.5 mm³ (125 nL), RF excitation pulse angle (α)=15° (500 μs, Gaussian shape) for HP propane-$d_6$ and α=2° (500 μs, Gaussian shape) for water phantom, total acquisition time of 17.7 s. No compressed sensing or other image acceleration technique was used, and no data manipulation was performed (i.e. zero-filling or smoothing). Percentage polarization of HP propane-$d_6$ gas was calculated as described earlier for HP propane gas and was estimated to be ~1% (19). It should be pointed out that this polarization estimate was done using spectroscopic detection of flowing HP propane with NMR FID of <100 ms (19). This is important, because spectroscopic method provides a more reliable number, because imaging of flowing propane gas at 4.7 T may suffer from significant MRI artifacts related to the fast flow and the encoding scheme (19). A spiral-shaped phantom was prepared using Tygon™ (3/32 in. ID×3/16 in. OD, McMaster Carr, Atlanta, Ga., P/N 5552K22) tubing wrapped around a plastic syringe to provide the dimensionality for imaging studies. Constant HP gas flow rate (~15 mL/min) was maintained during an entire 3D MRI scan.

For propane studies, the concentration of resulting propane gas was estimated to be ~20 mM based on the 1:1 ratio of residual parahydrogen and HP propane gas, room temperature of gas (~300 K) and 1 atm of total pressure. For imaging of water, the water phantom is prepared differently, where deionized water completely filled the spiral phantoms, with the inlet and outlet plugged. Polarization enhancement of HP propane at 4.7 T was calculated by performing a single scan NMR spectroscopy of flowing HP gas and water in the same phantom using previously described method (23). Calculated in this fashion % $P_H$ was ~1% per one methylene and one methyl protons $H_a$ and Hb shown in FIG. 1, part (B).

For HP propane low-field MRI experiments at 0.0475 T, the flow rate was stopped after ~1 s of initial gas flow, and the gas was allowed to condense resulting in final estimated total pressure of ~5 bar and estimated gas phase temperature of 373 K. Note that the gas was not cooled by a very short delivery path using the same tubing as in high-field 4.7 T studies described in the above paragraph. The reaction yield was estimated to be ~100% for calculation of % $P_H$ detected in the 0.0475 T inside approximately 2 mL cylindrical phantom. Note that the phantom contains a significantly wider cylindrical section seeing in FIG. 3, part (E) as a disc around the main phantom section.

All 0.0475 T experiments were conducted with Magritek (Wellington, New Zealand) instrumentation with on-site assembly. Custom 38 mm ID RF coils was used. The spectrum of HP propane was referenced to a spectrum of thermally polarized water using the same spectroscopic parameters and 45° RF excitation pulse. The polarization enhancement factor for propane was calculated as follows: $\epsilon=(S_{HP}\times\chi_{H2O})/(S_{H2O}\times\chi_{HP})\sim 10\,000$, where $S_{HP}$ and $S_{H2O}$ are integrated NMR signals of HP propane and thermally polarized water respectively, and $\chi_{H2O}$ and $\chi_{HP}$ are molar quantities of water and produced HP propane (calculated as estimated gas phase concentration of 82 mM at 2.5 bar partial pressure and 373 K temperature and multiplied by the phantom volume of ~2 mL). The resulting % $P_H$ of 0.16% of HP propane was calculated as the following: % $P_{HP}$=E×% $P_{THERMAL}$, where % $P_{THERMAL}$=1.6×10⁻⁷ or 1.6×10⁻⁵% at 0.0475 T (23).

All imaging parameters for 0.0475 T images shown in FIG. 3 are provided in the corresponding figure caption.

For HP propane-$d_6$ studies, all low-field studies were carried out using a Kea2 NMR spectrometer (Magritek, Wellington, New Zealand) with a custom-built frequency optimized dual-channel RF $^1H$—X probe similarly to HP propane studies (12). The flow rate was not controlled in low-field MR experiments due to experimental limitations. Hyperpolarization via hydrogenation of propane-$d_6$ was conducted at Earth magnetic field, and HP gas was transferred into ~2 mL phantom (estimated transfer time<0.3 s) placed inside the 0.0475 T NMR magnet (Magritek, Wellington, New Zealand). HP propane-$d_6$ (or propane) gas was allowed to flow for ~1 s time period, after which the flow was terminated, and the phantom chamber was filled with HP gas mixture (estimated 4.7 bar partial pressure of propane-$d_6$ (or propane) at ~100° C.—unlike in high-field experiments, the exiting gas was passing through a very short section (<20 cm) of heated tubing) containing ~150 mM HP propane-$d_6$ (or propane) corresponding to ~300 µmoles quantity.

NMR HP spectroscopic signals of propane-$d_6$ and propane were referenced to the NMR signal from thermally polarized $H_2O$ (2.8 g, ~160 mmoles, 55 M concentration, containing 5 mM $CuSO_4$). The enhancement factors $\epsilon$ were calculated by comparing the signal intensities and quantities of HP gas and thermally polarized reference sample of water as follows: $\epsilon=(S_{HP}\times\chi_{H2O})/(S_{H2O}\times\chi_{HP})$~6,000, where $S_{HP}$ and $S_{H2O}$ are the integrals of the NMR signals of HP propane-$d_6$ and water, respectively, and $\chi_{H2O}$ and $\chi_{HP}$ are molar quantities of water and HP propane-$d_6$ respectively. Percentage of proton polarization in HP propane-$d_6$ was computed using thermal equilibrium proton polarization at 0.0475 T of $P_H$=1.6×10$^{-7}$ or 1.6×10$^{-5}$% as follows: $P_{HP}$=$\epsilon$× $P_{THERMAL}$ yielding $P_{HP}$~0.1% per each (two per molecule) hyperpolarized nascent proton.

All NMR spectra were recorded using a 45° excitation rectangular shape RF pulse angle and one scan. 2D MRI experiment was conducted using non-slice-selective 2D GRE sequence as supplied by the manufacturer (Magritek, Wellington, New Zealand) using the following pulse sequence parameters: TE/TR=7.0/20 ms, acquisition time=6.4 ms, SW=5.0 kHz, RF excitation pulse (rectangular shape) $\alpha$=7° (6.0 µs), FOV=28×28 mm$^2$ using 32×32 imaging matrix with 2 dummy scans with the total imaging time of ~0.7 s. Imaging of HP propane-$d_6$ utilized a single average, and was repeated every 3 s, while imaging of water utilized 8 averages. All images from propane-$d_6$ utilized 1 average (NA), while image of water were recorded with NA=8. All images were interpolated to 1024×1024 pixels via zero-filling the data to enhance visual representation.

$^1$H NMR spectra for propane, propane-$d_6$ and [3-$^{13}$C] propane were calculated based on the conventional spin-density matrix formalism. For propane, the following parameters were used: $\delta$=0.899 ppm (methyl, 6H), $\delta$=1.336 ppm (methylene, 2H), $J_{HH}$=7.4 Hz. For $^{13}$C-labeled propane, $\delta(^{13}C)$=16.2 ppm and $^1J_{CH}$=125 Hz were used, with the two H atoms inherited from parahydrogen residing on the two unlabeled ($^{12}$C) carbons in the propane molecule. For propane-$d_6$, the vicinal couplings were $^3J_{HH}$=7.4 Hz, $^3J_{HD}$=1.12 Hz and $^3J_{DD}$=0.17 Hz, while for the geminal H-D couplings the value $^2J_{HD}$=2 Hz was used.

Evolution of spin density matrix in the external magnetic field was evaluated by diagonalizing the Hamiltonian matrix to find eigenstates and eigenenergies of the spin system. The spin density matrix was then converted to the eigenbasis, and its elements propagated in time using the respective differences in eigenenergies. Evolution under the action of hard pulses was evaluated by constructing and applying the corresponding rotation operators, with only $^1$H nuclei affected by the pulses. Two types of calculations were performed: 1) assuming that both reaction and NMR signal detection took place at the 0.0475 T field; 2) for reaction performed at the Earth's field followed by adiabatic sample transfer to 0.0475 T for NMR signal detection. The calculation results were found to be almost identical. The field sweep was incorporated, when required, by using a series of short free evolution intervals interleaved with small stepwise increments in the magnetic field. The number of intervals (100-1000) was increased until no further changes in the calculated spectra were observed. The FID was calculated based on the free evolution of the density matrix with periodic calculation of transverse magnetization for $^1$H nuclei, followed by Fourier transform to generate the spectrum. Relaxation effects were not included in the calculations.

In addition to propane, other hyperpolarized gases can be utilized using long-lived singlet or pseudo-singlet states of parahydrogen. The list below shows examples of suitable compounds, although additional possibilities exist due to C—C long chains, isomerization, atom substitution with different isotope (deuterium) of heteroatom (halogen):

1. Propane, propylene and cyclopropane;
2. Butane, butylene, isobutane, cyclobutane, cyclobutylene;
3. Pentane, pentene, cyclopentane, cyclopentene;
4. Hexane, hexane, cyclohexane, cyclohexene,
5. Other substituted (1-4) compounds: for example, bromopropane, chloropropane and other halocarbons.

Other unsaturated and saturated linear, branched and cyclic variants (alkanes, alkenes, and alkynes), isomers, and isotopomers of the above gases can also be used. The latter may include isotopic enrichment with deuterium, $^{13}$C and other isotopes.

Having thus described the different embodiments of a system and method, it should be apparent to those skilled in the art that certain advantages of the described method and apparatus have been achieved. It should also be appreciated that various modifications, adaptations, and alternative embodiments thereof may be made within the scope and spirit of the present invention. The invention is further defined by the following claims.

REFERENCES

1. J. H. Ardenkjaer-Larsen, B. Fridlund, A. Gram, G. Hansson, L. Hansson, M. H. Lerche, R. Servin, M. Thaning, K. Golman, Increase in signal-to-noise ratio of >10,000 times in liquid-state NMR. *Proc. Natl. Acad. Sci. U.S.A* 100, 10158 (2003).
2. D. Lilburn, G. E. Pavlovskaya, T. Meersmann, Perspectives of hyperpolarized noble gas MRI beyond 3He. *J. Magn. Reson.* 229, 173 (2012).
3. T. G. Walker, W. Happer, Spin-exchange optical pumping of noble-gas nuclei. *Rev. Mod. Phys.* 69, 629 (1997).
4. J. P. Mugler, T. A. Altes, Hyperpolarized 129Xe MRI of the human lung. *J. Magn. Reson. Imaging* 37, 313 (2013).
5. P. Nikolaou, A. M. Coffey, L. L. Walkup, B. M. Gust, N. Whiting, H. Newton, S. Barcus, I. Muradyan, M. Dabaghyan, G. D. Moroz, M. Rosen, S. Patz, M. J. Barlow, E. Y. Chekmenev, B. M. Goodson, Near-unity nuclear polarization with an 'open-source' 129Xe hyperpolarizer for NMR and MRI. *Proc. Natl. Acad. Sci. U.S.A* 110, 14150 (2013).
6. M. G. Pravica, D. P. Weitekamp, Net NMR Alighnment By Adiabatic Transport of Parahydrogen Addition Products To High Magnetic Field. *Chem. Phys. Lett.* 145, 255 (1988).
7. L. S. Bouchard, S. R. Burt, M. S. Anwar, K. V. Kovtunov, I. V. Koptyug, A. Pines, NMR imaging of catalytic hydrogenation in microreactors with the use of parahydrogen. *Science* 319, 442 (2008).
8. M. Carravetta, M. H. Levitt, Long-lived nuclear spin states in high-field solution NMR. *J. Am. Chem. Soc.* 126, 6228 (2004).
9. G. Pileio, M. Carravetta, E. Hughes, M. H. Levitt, The Long-Lived Nuclear Singlet State of 15N-Nitrous Oxide in Solution. *J. Am. Chem. Soc.* 130, 12582 (2008).

10. W. S. Warren, E. Jenista, R. T. Branca, X. Chen, Increasing Hyperpolarized Spin Lifetimes Through True Singlet Eigenstates. *Science* 323, 1711 (2009).
11. S. J. DeVience, R. L. Walsworth, M. S. Rosen, Preparation of Nuclear Spin Singlet States Using Spin-Lock Induced Crossing. *Phys. Rev. Lett.* 111, 5 (2013).
12. A. M. Coffey, M. L. Truong, E. Y. Chekmenev, Low-field MRI can be more sensitive than high-field MRI. *J. Magn. Reson.* 237, 169 (2013).
13. J. Kurhanewicz, D. B. Vigneron, K. Brindle, E. Y. Chekmenev, A. Comment, C. H. Cunningham, R. J. DeBerardinis, G. G. Green, M. O. Leach, S. S. Rajan, R. R. Rizi, B. D. Ross, W. S. Warren, C. R. Malloy, Analysis of Cancer Metabolism by Imaging Hyperpolarized Nuclei: Prospects for Translation to Clinical Research *Neoplasia* 13, 81 (2011).
14. R. H. McKee, D. Herron, M. Saperstein, P. Podhasky, G. M. Hoffman, L. Roberts, The Toxicological Properties of Petroleum Gases. *Int. J. Toxicol.* 33, 28S (2014).
15. M. E. Hayden, C. P. Bidinosti, E. M. Chapple, Specific absorption rates and signal-to-noise ratio limitations for MRI in very-low magnetic fields. *Concept Magnetic Res. A* 40A, 281 (2012).
16. B. De Coene, J. V. Hajnal, P. Gatehouse, D. B. Longmore, S. J. White, A. Oatridge, J. M. Pennock, I. R. Young, G. M. Bydder, MR of the brain using fluid-attenuated inversion recovery (FLAIR) pulse sequences. *Am. J. Neuroradiol.* 13, 1555 (1992).
17. B. M. Goodson, Nuclear magnetic resonance of laser-polarized noble gases in molecules, materials, and organisms. *J. Magn. Reson.* 155, 157 (2002).
18. M. Weiger, K. P. Pruessmann, A.-K. Bracher, S. Köhler, V. Lehmann, U. Wolfram, F. Hennel, V. Rasche, High-resolution ZTE imaging of human teeth. *NMR Biomed.* 25, 1144 (2012).
19. K. V. Kovtunov, D. A. Barskiy, A. M. Coffey, M. L. Truong, O. G. Salnikov, A. K. Khudorozhkov, E. A. Inozemceva, I. P. Prosvirin, V. I. Bukhtiyarov, K. W. Waddell, E. Y. Chekmenev, I. V. Koptyug, High-resolution 3D Proton Hyperpolarized Gas MRI Enabled by Parahydrogen and Rh/TiO2 Heterogeneous Catalyst. *Chem. Eur. J.* 20, 11636 (2014).
20. C. A. Meriles, D. Sakellariou, A. H. Trabesinger, V. Demas, A. Pines, Zero- to low-field MRI with averaging of concomitant gradient fields. *Proc. Natl. Acad. Sci. U.S.A.* 102, 1840 (2005).
21. S. Appelt, H. Kuhn, F. W. Hasing, B. Blumich, Chemical analysis by ultrahigh-resolution nuclear magnetic resonance in the Earths magnetic field. *Nature Phys.* 2, 105 (2006).
22. I. C. Ruset, L. L. Tsai, R. W. Mair, S. Patz, M. I. Hrovat, M. S. Rosen, I. Muradian, J. Ng, G. P. Topulos, J. P. Butler, R. L. Walsworth, F. W. Hersman, A system for open-access He-3 human lung imaging at very low field. *Concept Magnetic Res. B* 29B, 210 (2006).
23. K. W. Waddell, A. M. Coffey, E. Y. Chekmenev, In situ Detection of PHIP at 48 mT: Demonstration using a Centrally Controlled Polarizer. *J. Am. Chem. Soc.* 133, 97 (2011).
24. A. M. Coffey, R. V. Shchepin, K. Wilkens, K. W. Waddell, E. Y. Chekmenev, A Large Volume Double Channel 1H—X RF Probe for Hyperpolarized Magnetic Resonance at 0.0475 Tesla. *J. Magn. Reson.* 220, 94 (2012).
25. P. Nikolaou, A. M. Coffey, K. Ranta, L. L. Walkup, B. Gust, M. J. Barlow, M. S. Rosen, B. M. Goodson, E. Y. Chekmenev, Multi-Dimensional Mapping of Spin-Exchange Optical Pumping in Clinical-Scale Batch-Mode 129Xe Hyperpolarizers. *J. Phys. Chem. B* 118, 4809 (2014).
26. M. Goldman, H. Johannesson, O. Axelsson, M. Karlsson, Hyperpolarization of C-13 through order transfer from parahydrogen: A new contrast agent for MFI. *Magn. Reson. Imaging* 23, 153 (2005).
27. P. Bhattacharya, E. Y. Chekmenev, W. F. Reynolds, S. Wagner, N. Zacharias, H. R. Chan, R. Biinger, B. D. Ross, Parahydrogen-induced polarization (PHIP) hyperpolarized MR receptor imaging in vivo: a pilot study of 13C imaging of atheroma in mice. *NMR Biomed.* 24, 1023 (2011).
28. P. Bhattacharya, E. Y. Chekmenev, W. H. Perman, K. C. Harris, A. P. Lin, V. A. Norton, C. T. Tan, B. D. Ross, D. P. Weitekamp, Towards hyperpolarized 13C-succinate imaging of brain cancer. *J. Magn. Reson.* 186, 150 (2007).
29. E. Y. Chekmenev, J. Hovener, V. A. Norton, K. Harris, L. S. Batchelder, P. Bhattacharya, B. D. Ross, D. P. Weitekamp, PASADENA hyperpolarization of succinic acid for MRI and NMR spectroscopy. *J. Am. Chem. Soc.* 130, 4212 (2008).
30. N. M. Zacharias, H. R. Chan, N. Sailasuta, B. D. Ross, P. Bhattacharya, Real-Time Molecular Imaging of Tricarboxylic Acid Cycle Metabolism in Vivo by Hyperpolarized 1-C-13 Diethyl Succinate. *J. Am. Chem. Soc.* 134, 934 (2012).
31. R. V. Shchepin, A. M. Coffey, K. W. Waddell, E. Y. Chekmenev, Parahydrogen Induced Polarization of 1-13C-Phospholactate-d2 for Biomedical Imaging with >30,000,000-fold NMR Signal Enhancement in Water. *Anal. Chem.* 86, 5601 (2014).
32. R. V. Shchepin, W. Pham, E. Y. Chekmenev, Dephosphorylation and biodistribution of 1-13C-phospholactate in vivo. *J. Labelled Comp. Radiopharm.* 57, 517 (2014).
33. F. Reineri, A. Viale, S. Ellena, D. Alberti, T. Boi, G. B. Giovenzana, R. Gobetto, S. S. D. Premkumar, S. Aime, N-15 Magnetic Resonance Hyperpolarization via the Reaction of Parahydrogen with N-15-Propargylcholine. *J. Am. Chem. Soc.* 134, 11146 (2012).
34. T. Theis, Y. Feng, T. Wu, W. S. Warren, Composite and shaped pulses for efficient and robust pumping of disconnected eigenstates in magnetic resonance. *J. Chem. Phys.* 140, 7 (2014).
35. Y. N. Zhang, P. C. Soon, A. Jerschow, J. W. Canary, Long-Lived 1H Nuclear Spin Singlet in Dimethyl Maleate Revealed by Addition of Thiols. *Angew. Chem. Int. Ed.* 53, 3396 (2014).
36. T. Hughes-Riley, J. S. Six, D. M. L. Lilburn, K. F. Stupic, A. C. Dorkes, D. E. Shaw, G. E. Pavlovskaya, T. Meersmann, Cryogenics free production of hyperpolarized 129Xe and 83Kr for biomedical MRI applications. *J. Magn. Reson.* 237, 23 (2013).
37. L. L. Tsai, R. W. Mair, M. S. Rosen, S. Patz, R. L. Walsworth, An open-access, very-low-field MRI system for posture-dependent He-3 human lung imaging. *J. Magn. Reson.* 193, 274 (2008).
38. M. Mishkovsky, T. Cheng, A. Comment, R. Gruetter, Localized in vivo hyperpolarization transfer sequences. *Magn. Reson. Med.* 68, 349 (2012).
39. M. L. Truong, A. M. Coffey, R. V. Shchepin, K. W. Waddell, E. Y. Chekmenev, Sub-second Proton Imaging of 13C Hyperpolarized Contrast Agents in Water. *Contrast Media Mol. Imaging* 9, 333 (2014).
40. K. V. Kovtunov, D. A. Barskiy, R. V. Shchepin, A. M. Coffey, K. W. Waddell, I. V. Koptyug, E. Y. Chekmenev, Demonstration of Heterogeneous Parahydrogen Induced Polarization Using Hyperpolarized Agent Migration from Dissolved Rh(I) Complex to Gas Phase. *Anal. Chem.* 86, 6192 (2014).
41. P. Nikolaou, A. M. Coffey, L. L. Walkup, B. Gust, C. LaPierre, E. Koehnemann, M. J. Barlow, M. S. Rosen, B. M. Goodson, E. Y. Chekmenev, A 3D-Printed High Power Nuclear Spin Polarizer. *J. Am. Chem. Soc.* 136 1636 (2014).
42. P. Nikolaou, A. M. Coffey, L. L. Walkup, B. M. Gust, N. R. Whiting, H. Newton, I. Muradyan, M. Dabaghyan, K. Ranta, G. Moroz, S. Patz, M. S. Rosen, M. J. Barlow, E. Y. Chekmenev, B. M. Goodson, XeNA: An automated 'open-source' 129Xe hyperpolarizer for clinical use. *Magn. Reson. Imaging* 32, 541 (2014).
43. I. C. Ruset, S. Ketel, F. W. Hersman, Optical pumping system design for large production of hyperpolarized Xe-129. *Phys. Rev. Lett.* 96, 053002 (2006).
44. A. L. Zook, B. B. Adhyaru, C. R. Bowers, High capacity production of >65% spin polarized xenon-129 for NMR spectroscopy and imaging. *J. Magn. Reson.* 159, 175 (2002).
45. P. Nikolaou, A. M. Coffey, M. J. Barlow, M. Rosen, B. M. Goodson, E. Y. Chekmenev, Temperature-Ramped 129Xe Spin Exchange Optical Pumping. *Anal. Chem.* 86, 8206 (2014).
46. L. L. Walkup, J. C. Woods, Translational applications of hyperpolarized 3He and 129Xe. *NMR Biomed.*, DOI 10.1002/nbm.3151 (2014).
47. M. Sarracanie, B. D. Armstrong, J. Stockmann, M. S. Rosen, High speed 3D overhauser-enhanced MRI using combined b-SSFP and compressed sensing. *Magn. Reson. Med.* 71, 735 (2014).
48. W. Dominguez-Viqueira, W. Berger, J. Parra-Robles, G. E. Santyr, Litz Wire Radiofrequency Receive Coils for Hyperpolarized Noble Gas MR Imaging of Rodent Lungs at 73.5 mT. *Concept Magnetic Res. B* 37B, 75 (2010).
49. B. Feng, A. M. Coffey, R. D. Colon, E. Y. Chekmenev, K. W. Waddell, A pulsed injection parahydrogen generator and techniques for quantifying enrichment. *J. Magn. Reson.* 214, 258 (2012).

What is claimed is:

1. A method for preserving a long-lived state of hyperpolarized gas, the method comprising:
    (a) mixing parahydrogen gas with an unsaturated precursor in an absence of paramagnetic gases and impurities;
    (b) performing a chemical reaction of the unsaturated precursor with parahydrogen by passing the mixture prepared in step (a) over or through hydrogenation catalyst for molecular addition and without scrambling of parahydrogen hyperpolarization of the parahydrogen to the unsaturated precursor in a low magnetic field, so as to generate a hyperpolarized long-lived singlet state gas;
    (c) maintaining the hyperpolarization of the hyperpolarized long-lived singlet state gas produced in step (b) at the low magnetic field where the H—H spin-spin coupling (J-coupling) of nascent parahydrogen protons in a reaction product is greater than a difference of chemical shifts of these two protons in units of Hertz;
    (d) transporting the long-lived hyperpolarized long-lived singlet state gas to a low-field MRI scanner while maintaining the low magnetic field, and (e) performing a low-field MRI scan while continuing to expose the hyperpolarized long-lived singlet state gas to the low magnetic field, wherein the hyperpolarized long-lived singlet state gas is in a singlet state that has a relaxation time constant of at least 5 seconds.

2. The method of claim 1, wherein the unsaturated precursor is propene.

3. The method of claim 1, wherein the paramagnetic gas is $O_2$.

4. The method of claim 1, wherein the impurities include $Cu^{2+}$.

5. The method of claim 1, wherein the impurities include iron.

6. The method of claim 1, wherein step (b) is performed without scrambling of parahydrogen hyperpolarization.

7. The method of claim 1, wherein the low magnetic field is Earth magnetic field.

8. The method of claim 1, wherein the low magnetic field is 1-100 mT.

9. The method of claim 1, wherein the reaction product is propane or propane-$d_6$.

10. The method of claim 1, wherein the reaction product is any of butane, butylene, isobutane, cyclobutane, cyclobutylene or their deuterated variants.

11. The method of claim 1, wherein the reaction product is any of pentane, pentene, cyclopentane, cyclopentene or their deuterated variants.

12. The method of claim 1, wherein the reaction product is any of hexane, hexene, cyclohexane, cyclohexene or their deuterated variants.

13. The method of claim 1, wherein the high magnetic field is 1 T or lower.

14. The method of claim 1, wherein the reaction product includes hyperpolarized propane or propane-$d_6$.

15. The method of claim 1, wherein the relaxation time is longer than $T_1$.

* * * * *